United States Patent
English

(10) Patent No.: US 9,721,751 B2
(45) Date of Patent: Aug. 1, 2017

(54) ELECTRON MICROSCOPY SPECIMEN AND METHOD OF FABRICATION

(71) Applicant: The Board of Trustees of the Leland Stanford Junior University, Palo Alto, CA (US)

(72) Inventor: Timothy Stephen English, Derwood, MD (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 166 days.

(21) Appl. No.: 14/832,179

(22) Filed: Aug. 21, 2015

(65) Prior Publication Data

US 2017/0069457 A1    Mar. 9, 2017

Related U.S. Application Data

(60) Provisional application No. 62/040,459, filed on Aug. 22, 2014.

(51) Int. Cl.
*H01L 21/00*    (2006.01)
*H01J 37/20*    (2006.01)
(Continued)

(52) U.S. Cl.
CPC ........ *H01J 37/20* (2013.01); *C23C 16/45525* (2013.01); *C23C 16/50* (2013.01); *H01J 2237/2602* (2013.01)

(58) Field of Classification Search
USPC ........... 257/758, 760, 798, E27.001, E27.01, 257/E27.011
See application file for complete search history.

(56) References Cited

U.S. PATENT DOCUMENTS 4,139,668 A * 2/1979 Ward, III ................ H01J 37/20
                                                    428/138
7,112,790 B1 * 9/2006 Wang .................... G01N 23/04
                                                    250/304
(Continued)

OTHER PUBLICATIONS

Steven M. George, "Atomic Layer Deposition: An Overview", "Chemical Reviews", Feb. 12, 2009, pp. 111-131, vol. 110, No. 1, Publisher: American Chemical Society, Published in: US.
(Continued)

*Primary Examiner* — Bernard Souw
(74) *Attorney, Agent, or Firm* — Kaplan Breyer Schwarz, LLP

(57) ABSTRACT

A method for preparing plan-view transmission electron microscopy specimens is disclosed. The method employs isotropic vapor-phase etching in conjunction with one or more integrated etch-stop layers that give rise to a support membrane having a well-controlled, substantially uniform thickness. In some embodiments, the support membrane comprises an etch-stop layer that is formed using a high-precision formation process, such as atomic-layer deposition, oxidation, and the like. As a result, formation of the support membrane does not require additional processes, such as mechanical polishing or ion milling, to achieve its desired thickness. The method enables reduced specimen-preparation time, as well as simultaneous preparation of multiple specimens having large, uniformly thick areas for imaging.

20 Claims, 10 Drawing Sheets

(51) Int. Cl.
*C23C 16/455* (2006.01)
*C23C 16/50* (2006.01)

(56) References Cited

U.S. PATENT DOCUMENTS

| | | | | |
|---|---|---|---|---|
| 7,348,570 | B2* | 3/2008 | Allred, Jr. | H01J 37/20 250/440.11 |
| 2007/0131873 | A1* | 6/2007 | Allred | H01J 37/20 250/440.11 |
| 2007/0152253 | A1* | 7/2007 | Lee | H01L 21/31691 257/295 |
| 2014/0170857 | A1* | 6/2014 | Lang | H01L 21/6708 438/749 |
| 2015/0141267 | A1* | 5/2015 | Rothberg | C12Q 1/6869 506/2 |
| 2015/0141268 | A1* | 5/2015 | Rothberg | C12Q 1/6869 506/2 |
| 2016/0084761 | A1* | 3/2016 | Rothberg | G01N 21/6428 506/4 |
| 2016/0370291 | A1* | 12/2016 | Rothberg | C12Q 1/6874 |
| 2016/0370292 | A1* | 12/2016 | Rothberg | C12Q 1/6874 |

OTHER PUBLICATIONS

Gregory N. Parsons, et al., "History of atomic layer deposition and its relationship with the American Vacuum Society", "Journal of Vacuum Science and Technology A", Aug. 16, 2013, pp. 050818-1-050818-11, vol. 31, No. 5, Publisher: American Vacuum Society, Published in: US.

\* cited by examiner

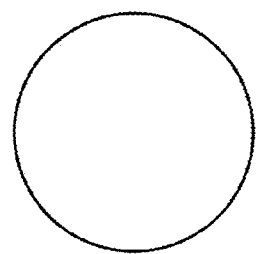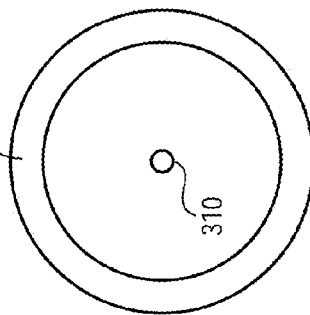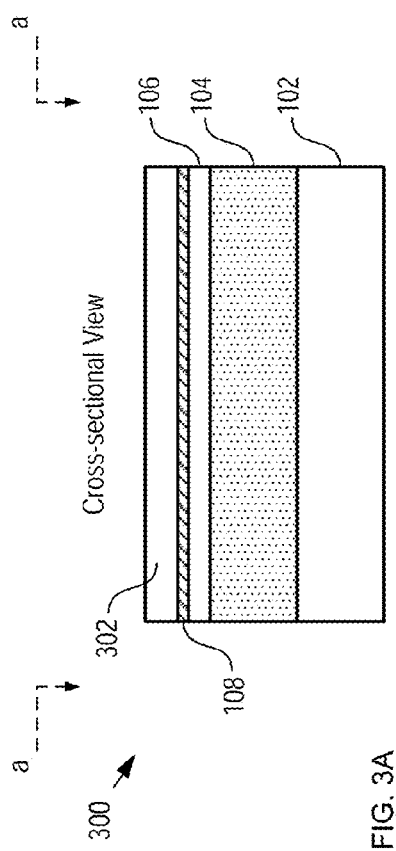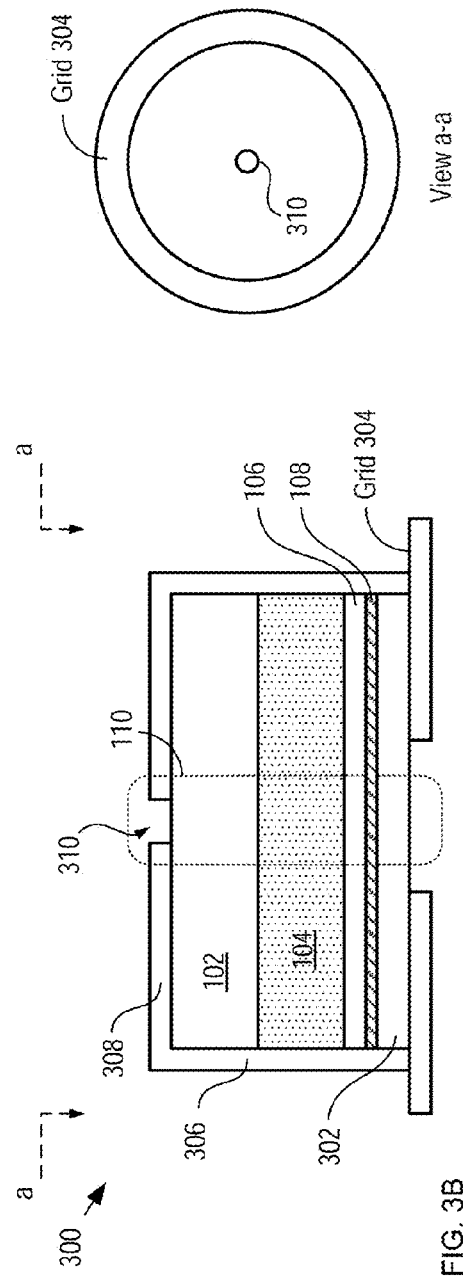
FIG. 3A
FIG. 3B

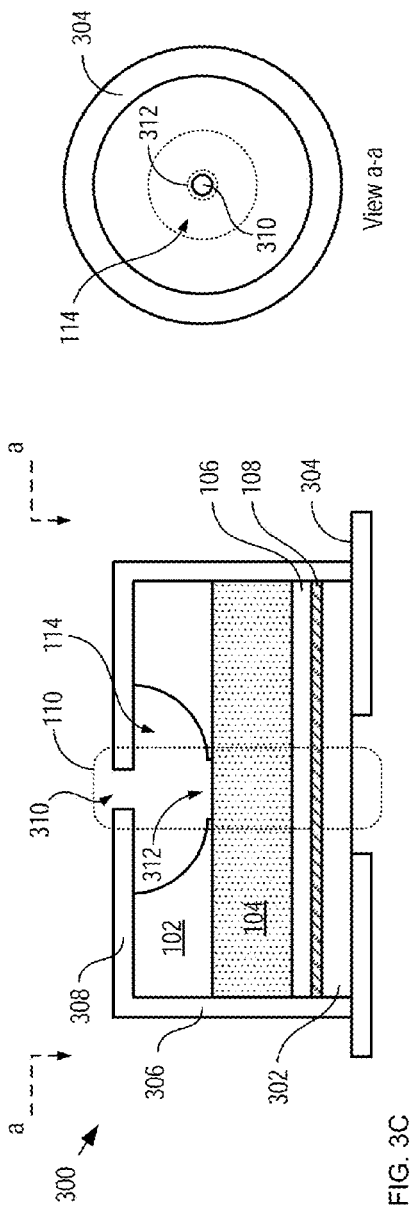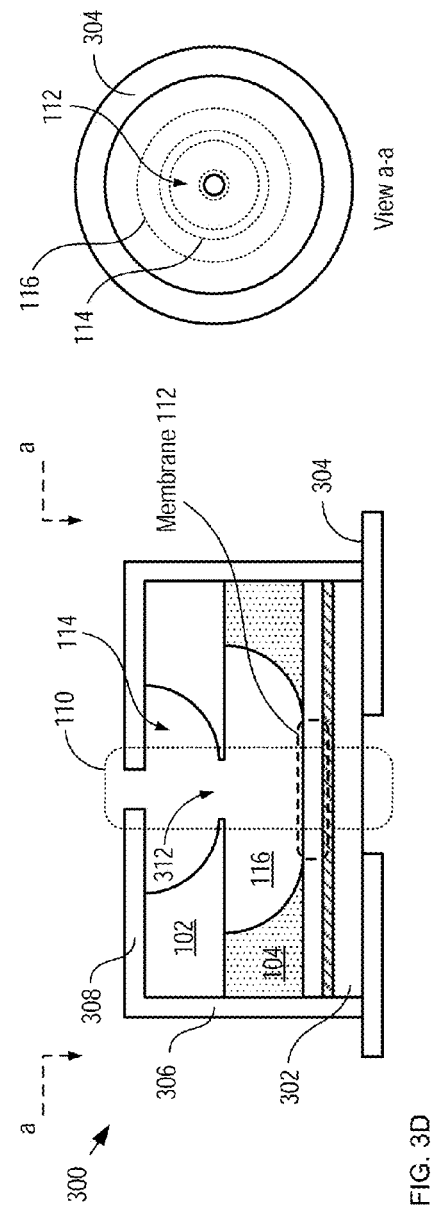

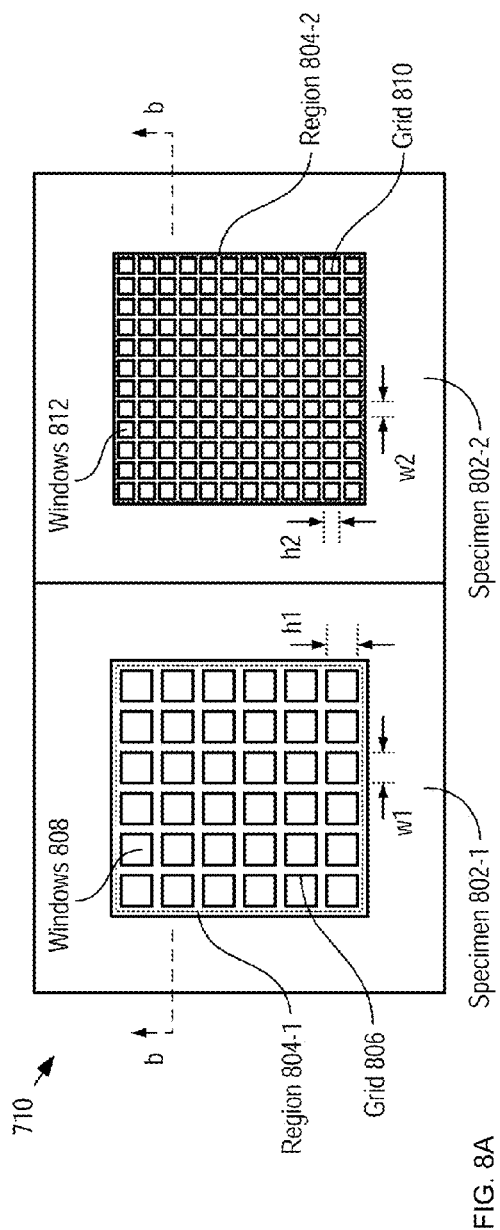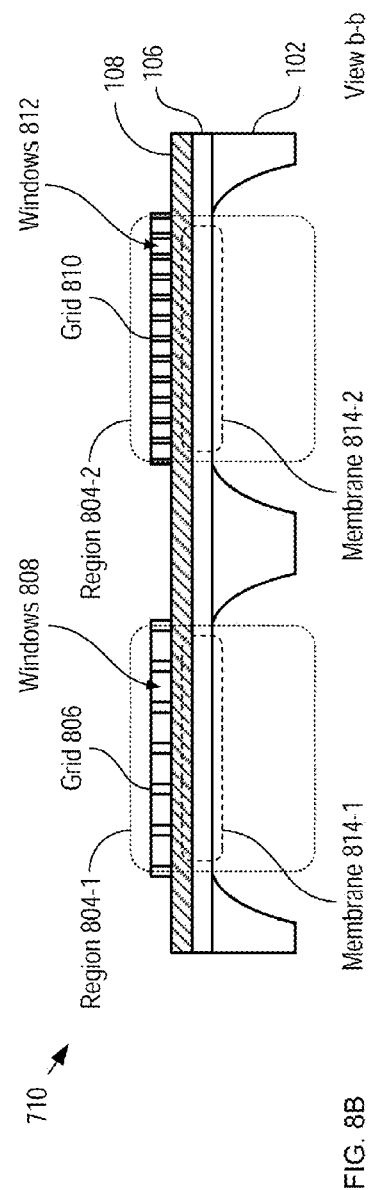
FIG. 8A
FIG. 8B

ELECTRON MICROSCOPY SPECIMEN AND METHOD OF FABRICATION

CROSS REFERENCE TO RELATED APPLICATIONS

This application claims the benefit of U.S. Provisional Application Ser. No. 62/040,459, filed Aug. 22, 2014, which is incorporated by reference. If there are any contradictions or inconsistencies in language between this application and one or more of the cases that have been incorporated by reference that might affect the interpretation of the claims in this case, the claims in this case should be interpreted to be consistent with the language in this case.

STATEMENT REGARDING FEDERALLY SPONSORED RESEARCH

This invention was made with Government support under contract N66001-10-1-4004 awarded by the Defense Advanced Research Projects Agency. The Government has certain rights in the invention.

FIELD OF THE INVENTION

The present invention relates to electron microscopy in general, and, more particularly, to electron microscopy specimen preparation.

BACKGROUND OF THE INVENTION

In microscopy, image resolution is based, in part, on the wavelength of the energy used to interrogate an object. Conventional optical microscopy uses visible light to form a magnified image of a specimen. As a result, the image resolution that can be obtained is fundamentally limited by the wavelength of visible light, which includes wavelengths from about 400 nanometers (nm) to about 700 nm. In electron microscopy, on the other hand, a specimen is interrogated with a beam of electrons. Electrons are characterized by a wavelength (i.e., the de Broglie wavelength) that is many orders of magnitude smaller than that of visible light; therefore, electron microscopy enables significantly improved image resolution as compared to optical microscopy. In fact, the ability to image fine detail has led to electron microscopy becoming a mainstay in many applications, such as sub-cellular structural analysis in biological specimens, determination of the crystal structure, structural analysis of thin films, etc., where the resolution of optical microscopy is insufficient.

Electron microscopy encompasses a number of techniques based on different material-electron interactions that give rise to the transmission, reflection, absorption, emission, interference and/or diffraction of the electrons as they interrogate the material. Images generated using electron microscopy can be a "traditional image" (analogous to a visible-light photograph) or a "non-traditional image," such as spectroscopic data that provides compositional information about the material. Perhaps the most ubiquitous electron microscopy technique capable of providing atomic resolution, however, is transmission Electron Microscopy (TEM). In TEM, electrons are transmitted through a thinned portion of a sample, referred to as a specimen. The specimen is typically disposed on a support membrane, although a specimen can be self-supported in some cases. As they pass through the specimen and support membrane, some of the electrons scatter and/or experience interference, giving rise to a "shadow image" of the specimen (and support membrane) in which sample structure manifests as varied contrast according to its density, thickness, or induced phase shift.

In order to obtain an image (traditional or non-traditional) of suitable quality, the material being imaged must be very thin and, ideally, of uniform thickness. One of the fundamental challenges in electron microscopy is the preparation required to form the thin specimen. Typically, specimens are prepared by hand or milled/ablated using a focused-ion beam (FIB) in conjunction with a precision mechanical stage and scanning electron microscope. Softer materials, such as biological samples, are typically sectioned using a glass or diamond edge to obtain a thickness within the range of a few nanometers to a few tens of microns. Specimens of harder materials, such as metals or semiconductor layers, are normally formed by thinning down a thick sample via the use of a physical and/or chemical subtractive process, such as etching, mechanical grinding, polishing, dimpling, ion milling, focused-ion-beam ablation, and the like. Unfortunately, conventional specimen preparation methods have several drawbacks.

First, conventional thinning processes are "blind" processes and, as a result, require frequent optical inspection to ensure the desired thinness is achieved and not exceeded. The removal of too much material often results in the specimen being damaged or destroyed. Prior-art specimen preparation methods provide no inherent protection against over-thinning of a sample. Further, not removing enough material can lead to substantial interference signals, during electron beam analysis, which can arise when the electron-beam-interaction volume contains a substantial volume-fraction of material other than the material of interest. Such interference signals can result, for example, from materials above (encapsulating material), or below (excess support structure), the material of interest, as well as laterally within the electron-beam-interaction volume.

Second, ideally, multiple prepared specimens of the same material-of-interest have the same thickness and are uniformly thin. Since specimens are generally prepared by hand and one at a time, however, variations in thickness and geometry within individual specimens are common and variation across different specimens can be significant. This can lead to undesirable imaging artifacts. Ion milling, for example, typically produces a wedge-shaped imaging region and thickness variations that can obscure features and produce artifacts in a resultant final image.

Third, the cost of specimen preparation in the prior art is extremely high due, in part, to the serial nature of conventional specimen preparation methods.

Fourth, many materials are not compatible with commercially available electron-microscopy grids that have pre-thinned support membranes. Vapor-phase-deposited materials, for instance, often deposit on all exposed surfaces—frontside and backside. This is particularly true for conformally deposited materials using deposition techniques such as atomic layer deposition (ALD), atomic layer epitaxy (ALE), other molecular layer deposition methods, vapor-phase epitaxy (VPE), metal-organic chemical vapor deposition (MOCVD), chemical-vapor deposition (CVD), low-pressure chemical-vapor deposition (LPCVD), plasma-enhanced chemical-vapor deposition (PECVD), etc. Although it is often possible to protect the back surface of a specimen membrane/grid during deposition using mechanical clamping, masking, etc., these solutions can be problematic and introduce issues with temperature stability, contamination, outgassing, induced stress, incompatibility with automated wafer handling and transport equipment, etc. In addition, the need for additional clamping/masking adds complexity and cost to the specimen preparation process.

A method for preparing large-area, very thin electron-microscopy specimens having precise and uniform thickness within a specimen, as well as across a plurality of specimens remains heretofore unrealized in the prior art.

SUMMARY OF THE INVENTION

The present invention enables preparation of electron-microscopy specimens having large, uniform-thickness imaging regions and enables multiple specimens to be prepared simultaneously, thereby overcoming the need for serial preparation of plan-view electron microscopy specimens as is practiced in the prior art. Embodiments of the present invention are well suited for use in preparing specimens for use in electron microscopy analysis in life-science and physical-science applications. Further, embodiments of the present invention are particularly well suited for use in the preparation of plan-view electron microscopy specimens of nanostructures and nanoparticles, such as clusters, powders, and crystals, as well as conformal and non-conformal material layers formed via vapor-deposition or growth techniques, such as ALD, ALE, VPE, MOCVD, CVD, LPCVD, PECVD, and the like. Still further, embodiments of the present invention are suitable for preparing specimens for use with nearly any electron microscopy technique, such as transmission electron microscopy, reflection electron microscopy, absorption electron microscopy, emission electron microscopy, interference electron microscopy, diffraction electron microscopy, and the like.

The present invention enables preparation of specimens and specimen support membranes having highly uniform thickness within individual specimens, as well as uniform thickness across different specimens. As a result, the present invention enables electron microscopy having improved electron-collection efficiency, which gives rise to improved signal-to-noise ratio (SNR). Further, the present invention enables parallel preparation of a plurality of specimens having substantially equal and uniform thickness. Such parallel preparation can be performed, for example, by simultaneously forming multiple specimens on a single substrate or planar-processing wafer.

An illustrative embodiment of the present invention employs a sacrificial layer of silicon dioxide on which an etch-stop layer of aluminum oxide is disposed. The etch-stop layer is formed using ALD, which enables precise control over its thickness and thickness uniformity. After forming a layer of a material of interest on the etch-stop layer, a region of the sacrificial layer under the etch-stop layer is removed using a first etch that substantially stops at the etch-stop layer. In the illustrative embodiment, a suitable first etch is a vapor-phase hydrofluoric acid etch. As a result, the etch-stop layer in the etched region functions as an ultrathin support membrane for the material of interest.

In some embodiments, multiple imaging regions are formed simultaneously on a single substrate. In some embodiments, specimen preparation is performed as part of wafer-scale fabrication. In some of these embodiments, one or more specimen regions are included within each of a plurality of device die regions located on a single substrate. In some embodiments, one or more imaging regions are included within each of a plurality of device test regions that is formed on a substrate comprising a plurality of device die.

In some embodiments, the etch-stop layer is formed via another deposition process that enables good thickness control, such as oxidation, ALE, chemical beam epitaxy (CBE), VPE, and the like.

In some embodiments, a second etch-stop layer is included. In some embodiments, the sacrificial layer is between the first and second etch-stop layers. In some embodiments, the sacrificial layer is the second etch-stop layer.

In some embodiments, an integrated support grid is included for providing mechanical support for the support membrane, thereby obviating the need to mount the specimen on a conventional electron microscopy sample grid.

An embodiment of the present invention is a method for forming one or more electron microscopy specimens on a substrate, the method comprising: providing the substrate such that includes a first sacrificial layer comprising a first material, the first material having a first etch rate in a first etchant; providing a first layer comprising a second material, the second material having a second etch rate in the first etchant, wherein the second etch rate is less than the first etch rate; providing the specimen, wherein the first layer is between the first sacrificial layer and the specimen; and removing the first material in a first region by exposing the first material to the first etchant, the first region comprising at least a portion of the specimen.

BRIEF DESCRIPTION OF THE DRAWINGS

FIGS. 3A-E depict cross-sectional and top views of specimen 100 at different stages of its fabrication.

FIGS. 8A-B depict top and cross-sectional views, respectively, of specimen region 710.

DETAILED DESCRIPTION

Figure 1:
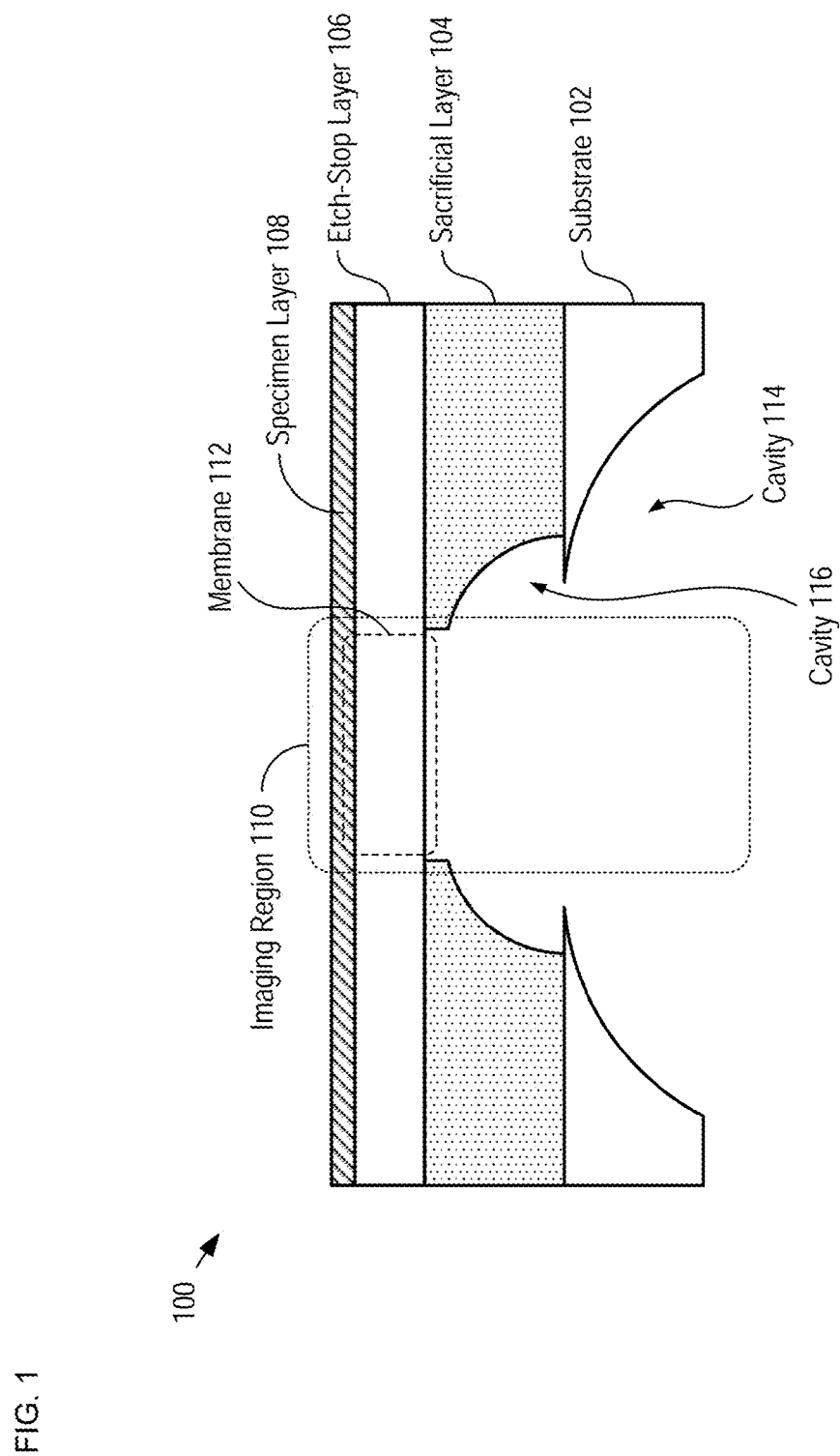
FIG. 1 depicts a schematic diagram of a cross-sectional view of an electron-microscopy specimen in accordance with an illustrative embodiment of the present invention.

FIG. 1 depicts a schematic diagram of a cross-sectional view of an electron-microscopy specimen in accordance with an illustrative embodiment of the present invention. Specimen 100 includes substrate 102, sacrificial layer 104, etch-stop layer 106, and specimen layer 108. Specimen 100 is an example of a specimen suitable for use in TEM; however, it will be clear to one of ordinary skill in the art, after reading this Specification, how to specify, make, and use alternative embodiments that are specimens suitable for use in any type of electron microscopy, such as reflection microscopy, absorption microscopy, emission microscopy, interference microscopy, diffraction microscopy, and the like.

Figure 2:
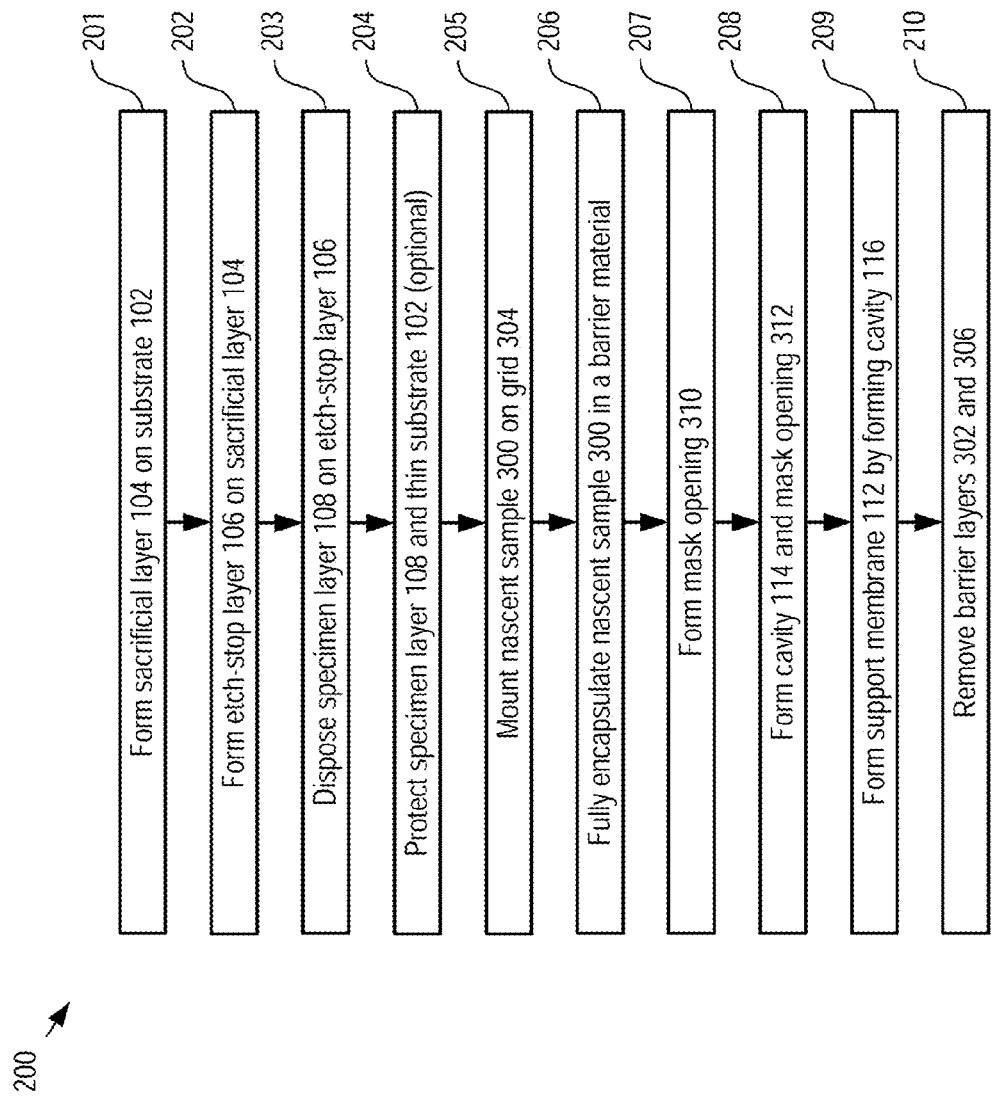
FIG. 2 depicts operations of a method for forming an electron-microscopy specimen in accordance with the illustrative embodiment.

FIG. 2 depicts operations of a method for forming an electron-microscopy specimen in accordance with the illustrative embodiment. Method 200 begins with operation 201, wherein sacrificial layer 104 is formed on substrate 102.

Substrate 102 is a substrate suitable for use in planar-processing fabrication. In the depicted example, substrate 102 is a conventional single-crystal silicon substrate; however, one skilled in the art will recognize, after reading this Specification, how to specify, make, and use alternative embodiments wherein substrate 102 is a different planar-processing substrate. Substrates suitable for use with the present invention include, semiconductor substrates (e.g., silicon, silicon germanium, silicon carbide, gallium arsenide, indium phosphide, gallium nitride, zinc selenide, etc.), metal substrates, ceramic substrates, glass substrates, and the like. In some embodiments, substrate 102 is an individual chip, die, or portion of a larger planar-processing wafer.

It should be noted that the present invention is suitable for use with substrates having a wide range of lateral dimensions. Typically, the lateral dimensions of substrate 102 are within the range of approximately 3 mm (i.e., the minimum size of a conventional TEM specimen) to several hundred mm (i.e., the diameter of conventional planar-processing wafers). As a result, the present invention enables wafer-scale integration of the specimen-preparation process.

Sacrificial layer 104 is a layer of material suitable for operation as: (1) an etch stop during the formation of cavity 114 in substrate 102; and (2) a sacrificial layer that facilitates the formation of cavity 116 that defines membrane 112, as discussed below. As a result, sacrificial layer 104 includes a material that is substantially unaffected by a first etchant used to remove substrate 102 in imaging region 110, but that can be readily removed in a second etchant that does not substantially etch etch-stop layer 106.

In the depicted example, sacrificial layer 104 is a layer of silicon dioxide that is thermally grown on substrate 102. Sacrificial layer 104 is grown to a thickness that is mechanically robust, but thin enough to facilitate its removal to expose specimen layer 108 in imaging region 110. In the illustrative embodiment, sacrificial layer 104 has a thickness of approximately 300 nm. Preferably, sacrificial layer 104 has a thickness that is less than two microns.

Although, in the illustrative embodiment, sacrificial layer 104 is thermally grown silicon dioxide, it will be clear to one skilled in the art, after reading this Specification, how to specify, make, and use alternative embodiments wherein sacrificial layer 104 comprises a different material formed using any suitable fabrication method.

At operation 202, etch-stop layer 106 is formed on sacrificial layer 104 via an atomic-layer-deposition process (ALD process) (i.e., etch-stop layer 106 is an atomic-layer-deposited layer). ALD processes suitable for use in embodiments of the present invention include, without limitation, atomic-layer epitaxy, atomic-layer chemical vapor deposition, molecular-layer deposition, molecular-layer epitaxy, molecular-beam epitaxy, chemical-beam epitaxy, binary reaction sequence chemistries, and the like. Examples of atomic-layer-deposition processes suitable for use in the present invention also include those ALD processes described in detail by S. M. George in "Atomic Layer Deposition: An Overview," *Chem. Rev., Vol.* 110, pp. 111-131 (2010), and by G. N. Parsons, et al., in "History of atomic layer deposition and its relationship with the American Vacuum Society," J. Vac. Sci. and Tech. A, Vol. 31 (2013), each of which is incorporated herein by reference. Etch-stop layer 106 functions as both an etch-stop layer during the removal of sacrificial layer 104 in imaging region 110, as discussed below, and as a mechanically robust support membrane 112 for specimen layer 108 after completion of specimen 100. As a result, etch-stop layer 106 comprises a material that can be used as a thin structural membrane, but that etches slowly, if at all, in an etchant suitable for etching sacrificial layer 104.

It is an aspect of the present invention that forming etch-stop layer 106 via an ALD process affords embodiments of the present invention with significant advantages over prior-art electron-microscopy structures. In particular, using an ALD process enables support membrane 112 to have a highly controllable and uniform thickness. Further, it enables support membranes whose thicknesses can be extremely thin—equal to or less than 50 nm. By keeping the thickness of support membrane 112 at or below 50 nm, membrane-related noise generation during electron microscopy is mitigated. As a result, the embodiments of the present invention enable electron microscopy with significantly higher signal-to-noise ratio, which further enables higher-resolution imaging than can normally be achieved in the prior art.

In the depicted example, etch-stop layer 106 is a layer of aluminum oxide having a thickness of approximately 10 nm. In some embodiments, etch-stop layer 106 comprises a material other than aluminum oxide, such as hafnium oxide ($HfO_2$), titanium oxide ($TiO_2$), zirconium oxide ($ZrO_2$), and nitrides including silicon nitride (SiN), tungsten nitride (WN), and titanium nitride (TiN), and their various stoichiometric phases. In some embodiments, etch-stop layer 106 has a thickness other than 10 nm. Typically, suitable thicknesses for etch-stop layer 106 are within the range of approximately 1 nm to approximately 100 microns and, preferably, less than 100 nm.

It is an aspect of the present invention that the use of an additive process for the formation of a support membrane provides a degree of membrane-thickness control not attainable with prior-art electron-microscopy specimen-preparation techniques. For the purposes of this Specification, including the appended claims, the term "additive process" is defined as a process wherein a layer of material is formed on a surface by the addition of matter. Examples of additive processes include oxidation, evaporation, and epitaxial growth. Additive processes are contrasted herein with subtractive processes, which reduce the thickness of a pre-existing layer by removal of matter from the layer (e.g., etching, polishing, lapping, etc.).

Because the quality of electron microscopy is directly related to the thickness of the support membrane on which the specimen is disposed, growing an ultrathin membrane by an additive process such as thermal oxidation and/or atomic layer deposition enables exceptionally high-quality imaging. Embodiments of the present invention, therefore, employ additive processes, such as thermal oxidation, ALD, ALE, MBE, VPE, MOCVD, CVD, LPCVD, PECVD, evaporation, and sputter deposition to form etch-stop layer 106 (i.e., support membrane 112). In addition to being characterized by a high degree of thickness control, many of these methods also enable real-time, in-situ thickness monitoring that further facilitates realizing a support membrane having a desired thickness and density and that is substantially free of pinholes.

On the other hand, subtractive methods for establishing the thickness of a support membrane, as are used in the prior art, are extremely difficult to control. As a result, prior-art electron microscopy specimens are plagued by poor thickness uniformity within individual specimen and significant thickness variation from specimen to specimen.

At operation 203, specimen layer 108 is disposed on etch-stop layer 106.

Specimen layer 108 is a layer of the material-of-interest. In the depicted example, specimen layer 108 is a layer of plasma-enhanced atomic-layer deposited platinum having a thickness of approximately 5 nm, which is grown directly on etch-stop layer 106. During the grown of specimen layer 108, etch stop layer 106 functions as a seed layer for the platinum. Although the illustrative embodiment includes a specimen structure for imaging a layer of polycrystalline platinum, it will be clear to one skilled in the art, after reading this Specification, how to specify, make, and use specimen structures suitable for analysis of any suitable specimen layer, including biological tissues, crystalline and non-crystalline thin films, etc. For the purposes of this Specification, including the appended claims, the term "biological tissue" is meant to include any biological matter suitable for electron-microscopy imaging, such as one or more cells, sub-cellular components (e.g., organelles, cell membranes, DNA, RNA, etc.), and other molecules having biological function.

It should be noted, however, that employing a support membrane that also acts as a seed layer for the growth of specimen layer 108 improves the ability to study nucleation effects, as well as other thin-film growth characteristics.

FIGS. 3A-E depict cross-sectional and top views of specimen 100 at different stages of its fabrication. In each of these figures, the top view of the specimen is view a-a, as depicted in the cross-sectional view.

FIG. 3A depicts cross-sectional and top views of nascent specimen 300 after the growth of specimen layer 108.

At optional operation 204, specimen layer 108 is protected by barrier layer 302 and substrate 102 is mechanically polished to a desired thickness. In the illustrative embodiment, substrate 102 is thinned to a thickness of approximately 200 microns; however, substrate 102 can have any suitable thickness. In the illustrative embodiment, barrier layer 302 comprises Crystalbond 509™; however, any suitable barrier material can be used for barrier layer 302.

At operation 205, nascent specimen 300 is inverted and mounted to conventional electron-microscopy grid 304. Grid 304 is typically an aluminum sample grid; however, one skilled in the art will recognize that any suitable material can be used for grid 304. In some embodiments, nascent specimen 300 is mounted on grid 304 prior to thinning substrate 102. In some embodiments, specimen 100 is mounted on grid 304 after the specimen has been completely prepared (i.e., after completion of method 200). In some embodiments, as discussed below, an integrated grid is included in the structure of a specimen, obviating grid 304 completely.

At operation 206, barrier layer 306 is formed over nascent specimen 300 to completely encapsulate it. The formation of barrier layer 306 gives rise to mask layer 308, which is disposed on the back surface of substrate 102 (i.e., the surface of the substrate distal to specimen layer 108). Protecting specimen 100 and, in particular, specimen layer 108, throughout the preparation process prevents exposure of the specimen of interest to harsh chemicals and/or abrasives, which can cause undesirable structural and chemical changes to the specimen. In some embodiments, nascent specimen 300 is encapsulated in a suitable material other than barrier material 302.

At operation 207, mask opening 310 is formed in mask layer 308. The formation of mask opening 310 exposes the back surface of substrate 102 within imaging region 110.

FIG. 3B depicts nascent specimen 300 after the formation of mask opening 310. It should be noted that, in FIGS. 3B-D, each view a-a shows nascent specimen 300 after it has been inverted and mounted on grid 304 with barrier layer 302 in contact with the grid.

At operation 208, cavity 114 is formed in substrate 102. Cavity 114 is formed by etching substrate 102 within imaging region 110, through mask opening 310. In the depicted embodiment, substrate 102 is etched using a first etch comprising xenon difluoride ($XeF_2$), which etches silicon substantially selectively over silicon dioxide. As the first etch proceeds through the thickness of substrate 102, therefore, it stops at the interface between substrate 102 and sacrificial layer 104. The formation of cavity 114 exposes a portion of sacrificial layer 104 within imaging region 110 such that the remaining substrate material functions as a second mask layer having mask opening 312.

FIG. 3C depicts nascent specimen 300 after the formation of cavity 114.

At operation 209, support membrane 112 is formed by etching sacrificial layer 104 through mask opening 312 to form cavity 116.

Sacrificial layer 104 is etched through mask opening 312 using a second etch that substantially selectively etches the sacrificial layer with respect to etch-stop layer 106. Typically, the second etch is also substantially selective for the sacrificial layer material with respect to the material of substrate 102 as well. In the depicted embodiment, the second etch comprises vapor-phase hydrofluoric acid (HF), which etches silicon dioxide substantially selectively over both silicon and aluminum oxide. As a result, the second etch proceeds through the thickness of sacrificial layer 104 but stops at etch-stop layer 106. The formation of cavity 116 removes all structural and sacrificial material from beneath etch-stop layer 106 in imaging region 110, thereby "releasing" it from its underlying layers. The released portion of etch-stop layer 106 defines support membrane 112.

FIG. 3D depicts completed specimen 100 after the formation of support membrane 112.

Methods in accordance with the present invention, such as method 200, enable large-area (e.g., >20,000 $\mu m^2$), very thin (e.g., <5-nm thickness), substantially uniform-thickness electron-microscopy specimens, thereby providing significant advantages over the prior art, including:
  i. improved electron-collection efficiency; or
  ii. improved signal-to-noise ratio; or
  iii. mitigated interference that arises from extraneous non-sample material in a specimen by enabling large-area membranes having uniform-thickness, nanometer-scale etch-stop support layers; or
  iv. any combination of i, ii, and iii.

It should be noted that, while wet-chemical etches can be used to etch sacrificial layer 104 and form support membrane 112, the use of a vapor-phase etch for this purpose affords embodiments of the present invention with several advantages over the prior art, including:
  i. reduced preparation time; or
  ii. reduced use of consumables; or iii. simultaneous fabrication of multiple specimens (i.e., parallel specimen preparation) due to the high selectivity that can be obtained, which allows for overetching of sacrificial layer 104 without degrading the quality of etch-stop layer 106, thereby providing a large, uniformly thin area for imaging; or iv. prevention of "in-process stiction" of support membrane 112; or v. wider selection of compatible materials for etch-stop layer 106 due to improved etch selectivity; or vi. any combination of i, ii, iii, iv, and v.

It should be further noted that $XeF_2$ and/or vapor-phase HF are only two examples of etchants that can have suitable selectivity for use in embodiments of the present invention. One skilled in the art will recognize, after reading this Specification, that a variety of etchants can be used to realize high etch selectivity between dielectrics, metals, and polymers, in conjunction with one or more etch stop layers, without departing from the scope of the present invention.

At operation 210, barrier layers 302 and 306 are removed in conventional fashion. The manner in which the barrier material is removed is based on the barrier material itself—for example, Crystalbond 509™ is typically removed by exposure to either a liquid- or vapor-phase organic solvent, such as acetone. In some embodiments, the removal of barrier layers 302 and 306 is performed such that a portion of barrier layer 302 remains as anchor 314, which serves to keep specimen 100 mounted on grid 304.

One skilled in the art will recognize, after reading this Specification, that, in some cases, it is not necessary to completely remove barrier layers 302 and 306 in operation 210, since high-quality imaging is possible through thin layers of some barrier materials. Further, in some embodiments, anchors 314 are not included for joining specimen 100 and grid 304.

Figure 3E:
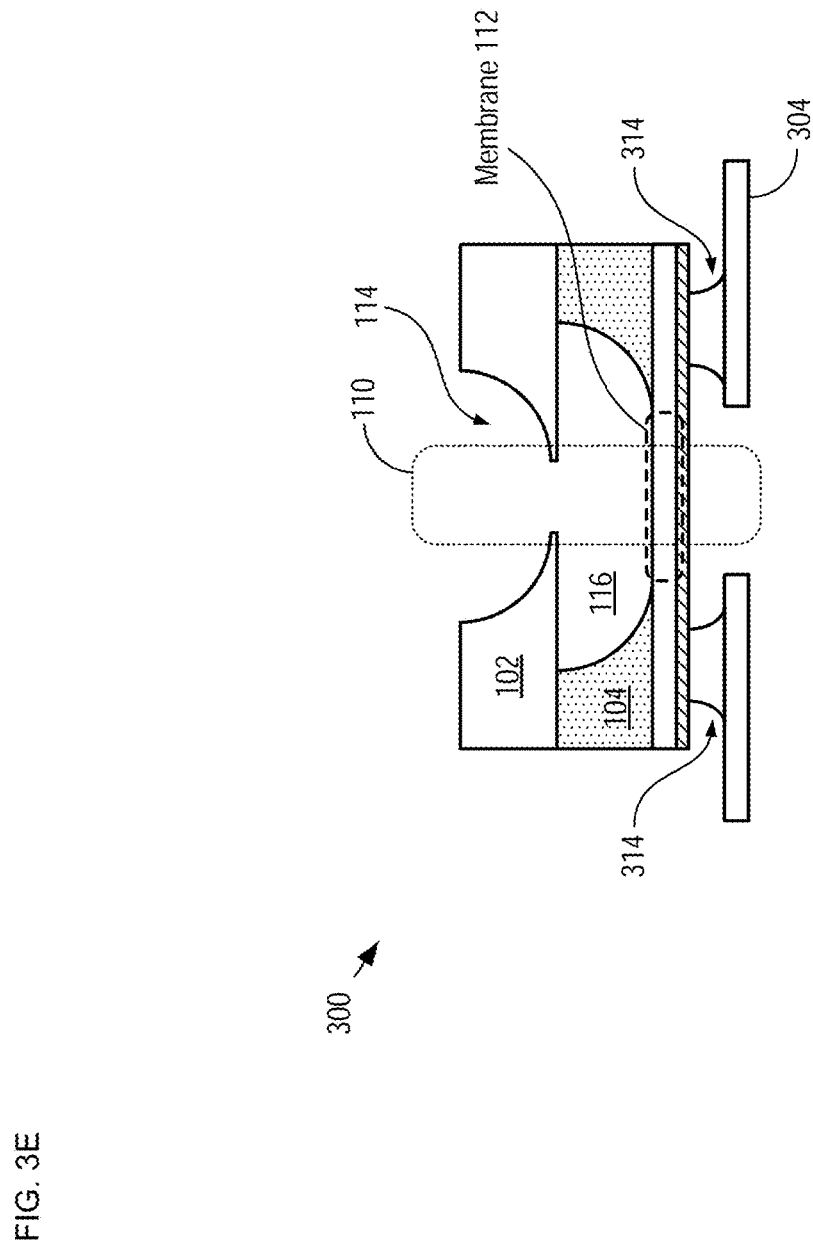

FIG. 3E depicts completed specimen 100 after operation 210.

Figure 4B:
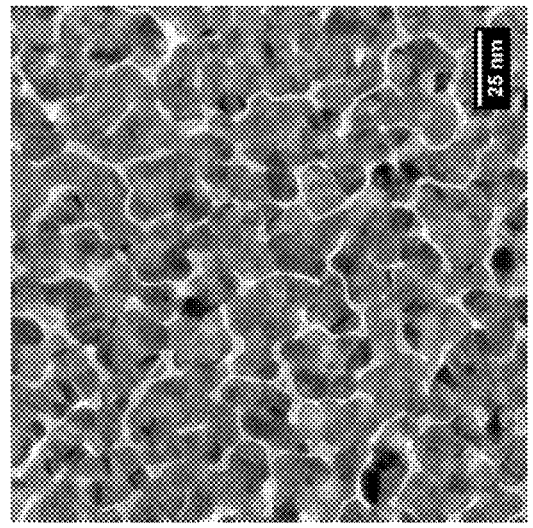
FIGS. 4A-B depict plan-view TEM images of specimens prepared using a conventional method and a method in accordance with the present invention, respectively.
Figure 4A:
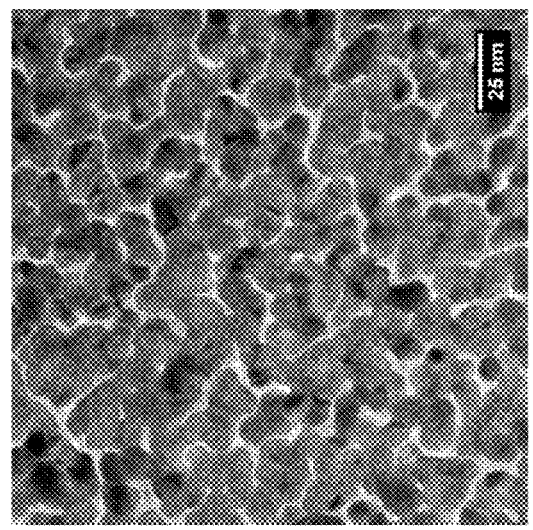

FIGS. 4A-B depict plan-view TEM images of specimens prepared using a conventional method and a method in accordance with the present invention, respectively. Specimen 400 is a specimen prepared using conventional preparation methods. Specimen 402 is a specimen prepared using a method in accordance with the present invention.

The combination of the use of a highly selective etch and an etch-stop layer that is formed using a growth or deposition process represents a substantially self-limiting fabrication process. As a result, embodiments of the present invention enable fabrication of specimens having consistent support membrane geometries that can be repeatedly realized from specimen to specimen and from study to study, thereby minimizing imaging artifacts due to inadvertent differences in the specimen geometry itself.

Further, many vapor-phase etchants are effective at room temperature. As a result, methods in accordance with the present invention can be carried out at relatively low temperatures, which is required in many applications, such as the preparation of life-science specimens.

While commercially available transmission electron microscopy grids with pre-thinned membranes are available, they are not always suitable or even desirable. In cases where a specimen is formed using a conformal deposition technique (e.g., atomic-layer deposition, atomic-layer epitaxy, and molecular layer deposition, etc.), grids with pre-thinned membranes are unsuitable. Specifically, the conformal nature of these deposition techniques results in deposition onto both the front and backside surfaces of a membrane. There are conventional methods to prevent deposition onto both membrane faces, including mechanical clamping and masking structures; however, these solutions are not always viable and typically are not desirable due to limited temperature stability, introduction of contamination into the deposition environment, outgassing, significant topology differences introduced by the mask itself, and incompatibility with automated wafer handling and transport equipment.

Although the illustrative embodiment employs multiple etch-stop layers, it will be clear to one skilled in the art, after reading this Specification, how to specify, make, and use alternative embodiments wherein only one (or more than two) etch-stop layers are used.

Figure 5:
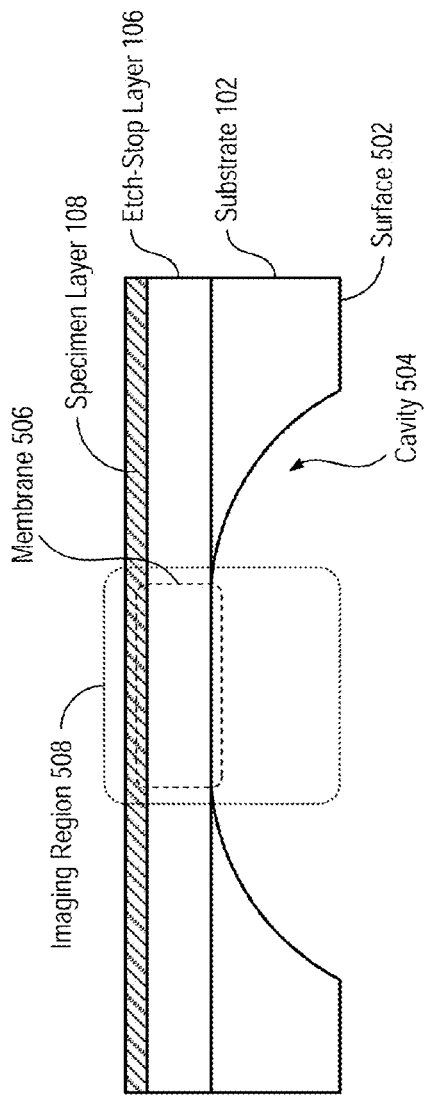
FIG. 5 depicts a schematic diagram of a cross-sectional view of a specimen in accordance with a first alternative embodiment of the present invention.

FIG. 5 depicts a schematic diagram of a cross-sectional view of a specimen in accordance with a first alternative embodiment of the present invention. Specimen 500 includes substrate 102, etch-stop layer 106, and specimen layer 108.

Figure 6:
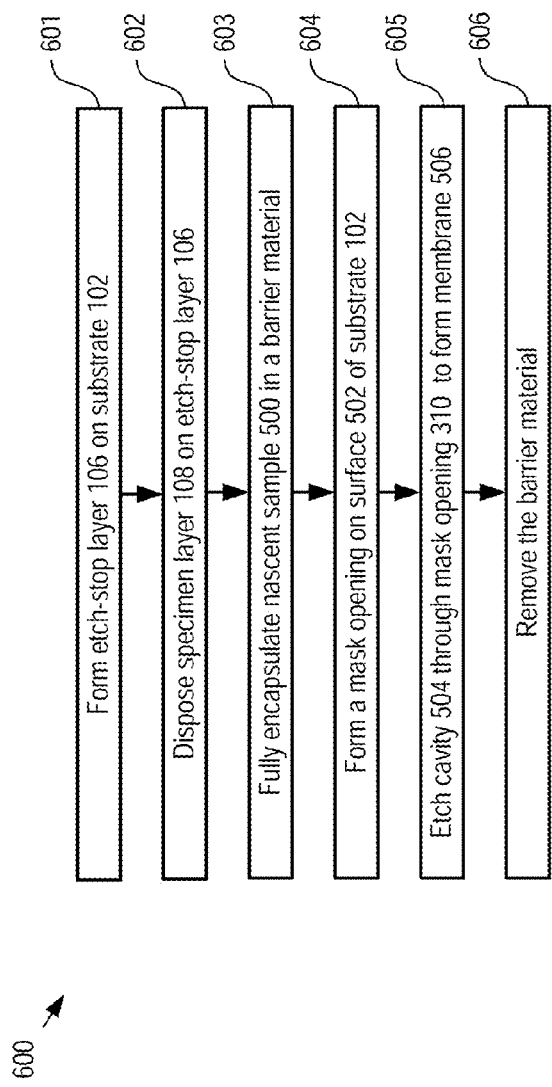
FIG. 6 depicts operations of a method for forming specimen 500.

FIG. 6 depicts operations of a method for forming specimen 500. Method 600 begins with operation 601, wherein etch-stop layer 106 is formed on substrate 102.

At operation 602, specimen layer 108 is disposed on etch-stop layer 106.

At operation 603, nascent specimen 500 is encapsulated in barrier material, as described above and with respect to operations 204 and 206 of method 200.

At operation 604, a mask opening is formed to expose a portion of surface 502 of substrate 102, as described above and with respect to operation 207 of method 200.

At operation 605, cavity 504 is formed by etching substrate 102 through the mask opening formed in operation 604. The formation of cavity 504 defines membrane 506 in imaging region 508 and results in fully formed specimen 500.

At operation 606, the barrier material is removed from specimen 500, as described above and with respect to operation 210 of method 200.

Although each of the illustrative embodiment and first alternative embodiment comprises a single etch-stop layer, it will be clear to one skilled in the art, after reading this Specification, how to specify, make, and use alternative embodiments that include more than one etch-stop layer. The use of multiple etch-stop layers can reduce preparation time, as well as enable the use of a wider range of materials and etchants.

As discussed above, although the illustrative embodiment is an individual specimen, in some embodiments, multiple specimen can be prepared simultaneously on the same substrate using wafer-level fabrication techniques. An ability to perform specimen preparation at wafer scale on full-size wafers (i.e., wafers suitable for CMOS processing, etc.) affords embodiments of the present invention with several advantages over the prior art. For example, methods disclosed herein are compatible with automated wafer handling equipment. In contrast, conventional specimen preparation is typically done on individual chips whose size is based on compatibility with electron microscopy equipment and, therefore, are not compatible with such equipment.

Still further, compatibility with wafer-scale processing enables specimens to be fabricated with other structures on the same substrate. For example, electron-microscopy samples can be disposed on the same substrate as test structures for analyzing electrical, optical, magnetic, and/or thermal properties and/or behavior. This enables a broad set of static and/or dynamic materials analysis that can even be conducted in-situ during electron microscopy.

It should be noted that conventional sample grids and mounts, as well as substrate pieces, typically have particulate and cleanliness issues that preclude their introduction into a cleanroom. In contrast, methods in accordance with the present invention are compatible with a cleanroom environment. In some embodiments, a sample grid is integrated into a specimen in order to mitigate the particulate and cleanliness issues associated with the use of conventional sample grids.

Figure 7B:
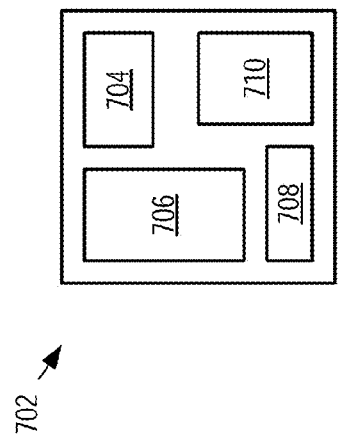
FIG. 7B depicts a schematic diagram of a test chip in accordance with the second alternative embodiment.
Figure 7A:
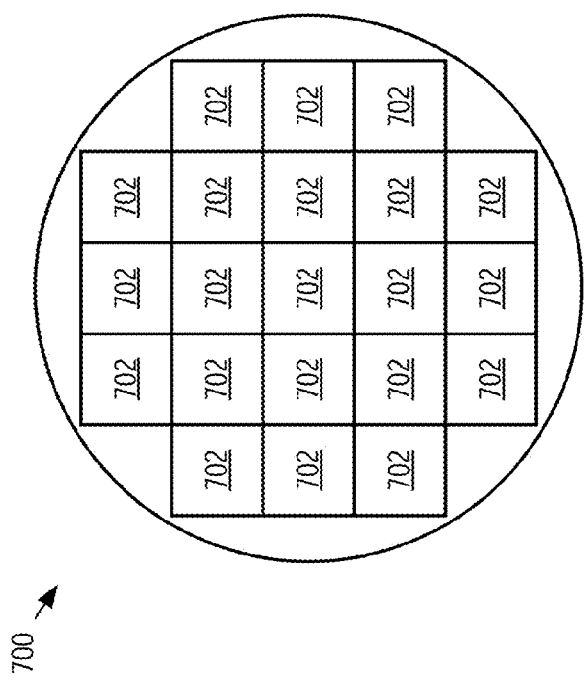
FIG. 7A depicts a schematic diagram of a top view of substrate comprising a plurality of multi-parameter test chips that include electron-microscopy specimens in accordance with a second alternative embodiment of the present invention.

FIG. 7A depicts a schematic diagram of a top view of substrate comprising a plurality of multi-parameter test chips that include electron-microscopy specimens in accordance with a second alternative embodiment of the present invention. Substrate 700 includes a plurality of substantially identical test chips 702.

FIG. 7B depicts a schematic diagram of a test chip in accordance with the second alternative embodiment. Test chip 702 includes mechanical test region 704, electrical test region 706, optical test region 708, and specimen region 710.

Each of regions 704, 706, and 708 includes conventional test devices suitable for performing static and dynamic mechanical, electrical, and optical testing, respectively, of a material of interest.

Specimen region 710 is described in detail below and with respect to FIGS. 8A-B.

FIGS. 8A-B depict top and cross-sectional views, respectively, of specimen region 710. The cross-sectional view shown in FIG. 8B is taken through line b-b shown in FIG. 8A. Specimen region 710 includes imaging regions 804-1 and 804-2, each of which is analogous to imaging region 110 described above; however, each imaging region of specimen region 710 further includes an integrated support grid.

A specimen region 710 is simultaneously formed on each of chips 702, using wafer-scale fabrication. Each of imaging regions 804 is analogous to imaging region 110 described above. In some embodiments, at least one of imaging regions 804 has a support membrane of a different lateral size.

In imaging region 804-1, membrane 814-1 supports a first portion of specimen layer 108, as described above and with respect to FIG. 5. Imaging region 804-1 also includes support grid 806, which is disposed on specimen layer 108 and dimensioned and arranged to add mechanical strength to imaging region 804-1.

Support grid 806 is a lattice of structural material having a plurality of horizontal lines and vertical lines (as shown). The lattice arrangement of support grid 806 defines a plurality of windows 808, each of which has lateral dimensions w1 and h1. For exemplary purposes, in the depicted example, each of w1 and h1 is equal to 25 microns.

In similar fashion, in imaging region 804-2, membrane 814-2 supports a second portion of specimen layer 108. Imaging region 804-2 includes support grid 810, which is disposed on specimen layer 108 and dimensioned and arranged to add mechanical strength to imaging region 804-2. Support grid 810 is analogous to support grid 806.

Support grid 810 is a lattice of structural material having a plurality of horizontal lines and vertical lines (as shown), which are on a different spacing from those of support grid 806. The lattice arrangement of support grid 810 defines a plurality of windows 812, each of which has lateral dimensions w2 and h2. For exemplary purposes, in the depicted example, each of w2 and h2 is equal to 8 microns.

In some embodiments, the mechanical strength added to imaging regions 804-1 and 804-2 by the addition of support grids 806 and 810, respectively, obviates the need for mounting specimen region 710 on a conventional electron-microscopy sample grid.

Each of support grids 806 and 810 is disposed on its respective membrane via a conventional lift-off process; however, one skilled in the art will recognize that this is only one of myriad processes to form the support grids without departing from the scope of the present invention. Each of support grids 806 and 810 comprises a structural material having sufficient strength for reinforcing its respective membrane. In some embodiments, the material selected for support grids 806 and 810 is characterized by residual tensile stress to facilitate release of the membranes without breakage. Preferably, however, the material used for the support grids is characterized by low residual stress to mitigate its effect on the material of specimen layer 108. Materials suitable for use for support grids 806 and 810 include, without limitation, silicon nitride, metals, semiconductors (e.g., silicon, silicon carbide, silicon germanium, gallium arsenide, indium phosphide, etc.), and the like. In the depicted example, each of support grids 806 and 810 comprises conventional bond pad metallization.

In some embodiments, at least one of support grids 806 and 810 comprises a material that is suitable for use as a reference material during electron microscopy. For example, a support grid can comprise a material having known structural and chemical properties suitable for use for calibration purposes during TEM analysis. In some embodiments, at least one of support grids 806 and 810 comprises a suitably crystalline material having a known lattice constant, thereby providing an integrated reference that can be directly measured for absolute scale calibration. Although specimen region 710 includes two imaging regions having different numbers and sizes of windows, it will be clear to one skilled in the art, after reading this Specification, how to specify, make, and use alternative embodiments wherein a specimen region includes any practical number of imaging regions having any practical number of windows of any practical size.

Figure 9:
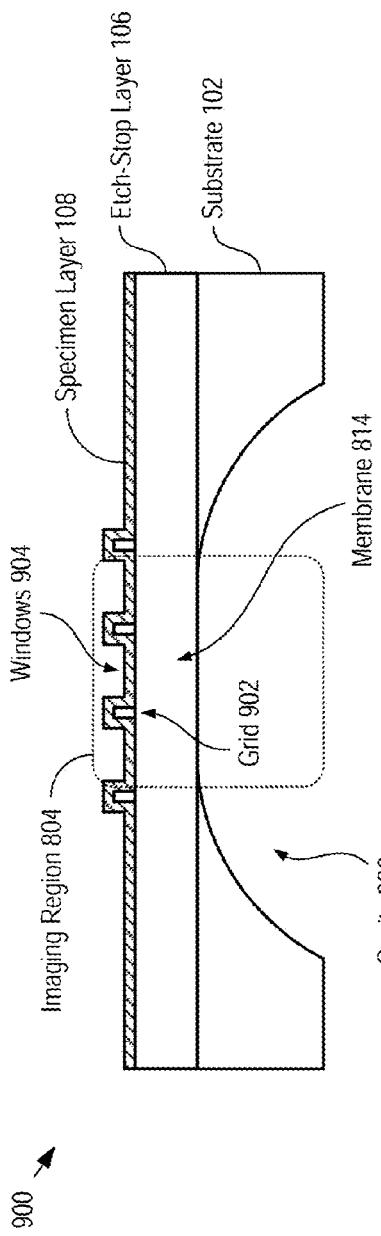
FIG. 9 depicts a schematic drawing of a cross-sectional view of a specimen in accordance with a third alternative embodiment.

FIG. 9 depicts a schematic drawing of a cross-sectional view of a specimen in accordance with a third alternative embodiment. Specimen 900 comprises substrate 102, etch-stop layer 106, support grid 902, and cavity 906, which defines membrane 814 in imaging region 804, as described above and with respect to FIGS. 8A-B. Specimen 900 is analogous to specimens 802-1 and 802-2; however, support grid 902 is formed on etch-stop layer 106 prior to the deposition of specimen layer 108.

Figure 10:
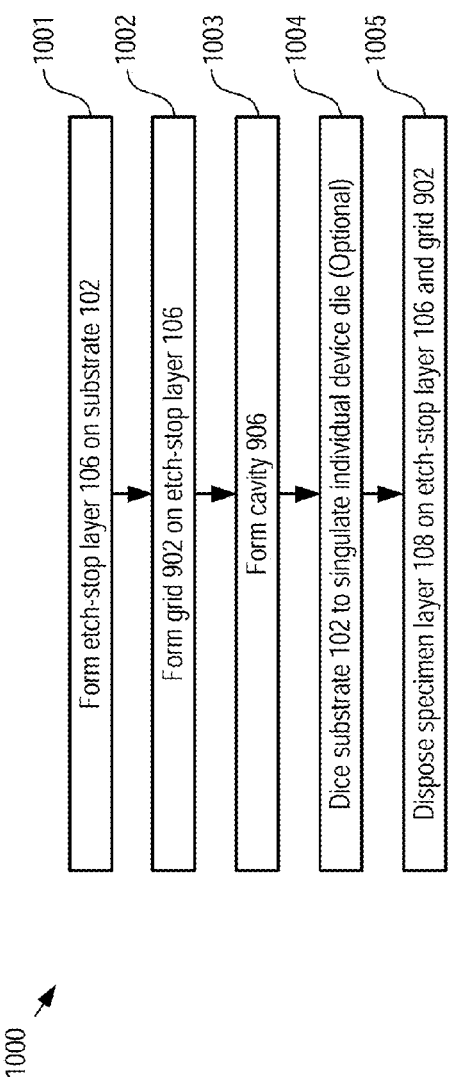
FIG. 10 depicts salient operations of a method for forming specimen 900.

Support grid 902 is analogous to support grids 806 and 810 described above. The lattice arrangement of support grid 902 defines a plurality of windows 904, FIG. 10 depicts salient operations of a method for forming specimen 900. Method 1000 is analogous to method 600 described above; however, in method 1000, support grid 902 is formed prior to the deposition of specimen layer 108 and, typically, before the etching of cavity 906. As a result, within imaging region 804, specimen layer 108 is disposed on etch-stop layer 106 only in windows 904. Preferably, grid 902 comprises a material resistant to the etchant used to form cavity 906 and can, therefore, be formed before definition of the cavity. In some embodiments, a barrier layer (e.g., barrier layer 302) is formed over grid 902 prior to the definition of cavity 906 to mitigate exposure of specimen layer 108 and grid 902 to harsh chemicals and/or abrasives, including the etchant used to form cavity 906.

Embodiments wherein the support grids are formed prior to deposition of the specimen layer provide an advantage in that multiple support membranes and support grids can be fully formed on the same wafer using wafer-scale fabrication. Once the membranes and support grids are fully defined on the wafer, it can be singulated (e.g., diced, sawed, cleaved, etc.) into individual device die. As a result, specimen layers can be deposited or grown on individual device die at the chip level. This enables different specimen layers on different device die, for example. Further, it enables specimen layer deposition techniques that are not wafer-level-process compatible to be employed.

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. A method for forming one or more electron microscopy specimens on a substrate, the method comprising:
providing the substrate comprising a first material, the first material having a first etch rate in a first etchant;
forming a first layer on a first surface of the substrate, wherein the first layer is formed via an atomic-layer-deposition process, and wherein the first layer comprises a second material having a second etch rate in the first etchant, and further wherein the second etch rate is slower than the first etch rate;
disposing a first specimen on the substrate in a first region such that the first layer is between the substrate and the specimen; and
forming a first support membrane in the first region by exposing the first material in the first region to the first etchant, the first support membrane comprising a first portion of the first layer.

2. The method of claim 1 wherein the atomic-layer deposition process is selected from the group consisting of atomic-layer deposition, atomic-layer epitaxy, atomic-layer chemical-vapor deposition, molecular-beam deposition, molecular-beam epitaxy, chemical-beam epitaxy, and binary-reaction-sequence chemistry.

3. The method of claim 1 further comprising:
providing the substrate such that it includes a second layer and a first sacrificial layer that comprises the first material and the first surface, the first sacrificial layer being between the second layer and the first layer; and
exposing a second surface of the first sacrificial layer in the first region by forming a first cavity in the second layer.

4. The method of claim 3 wherein the second layer is at least a portion of a silicon wafer suitable for planar processing and the first sacrificial layer comprises a silicon oxide.

5. The method of claim 3 wherein the first cavity is formed by operations comprising:
providing the second layer such that it comprises a third material;
forming a mask feature that exposes a third surface of the second layer in the first region, the third surface being distal to the second surface; and
exposing the third surface to a second etchant that etches the third material faster than the first material.

6. The method of claim 1 further comprising forming a support grid in the first region, the support grid being operative for supporting the first support membrane.

7. The method of claim 1 further comprising forming third layer that is operative for inhibiting exposure of the specimen to the first etchant in the first region.

8. The method of claim 1 wherein the first specimen comprises biological tissue, and wherein the third layer is formed prior to removing the first material in the first region.

9. A method for forming one or more electron microscopy specimens on a substrate, the method comprising:
forming a first etch-stop layer on the substrate, wherein the first etch-stop layer is formed via an additive process, and wherein the substrate comprises a first material and the first etch-stop layer comprises a second material, and further wherein the first etch-stop layer has a thickness that is less than or equal to 50 nanometers;
providing a specimen layer that is disposed on the first etch-stop layer; and
forming a first support membrane in a first region by exposing the first region to a first etchant that etches the first material at a faster rate than the second material, wherein the first support membrane comprises a first portion of the first etch-stop layer.

10. The method of claim 9 further comprising removing the first material within a second region by exposing the substrate to the second etchant, wherein first region and second region are exposed to the first etchant at the same time.

11. The method of claim 9 further comprising:
providing the substrate such that it comprises a first layer and a second layer, the first layer comprising the first material and the second layer comprising a third material, wherein the first layer is between the second layer and the first etch-stop layer; and
removing the third material from the first region by exposing the substrate to a second etchant in the first region, wherein the second etchant etches the third material at a faster rate than the first material.

12. The method of claim 9 further comprising forming a support grid on the substrate, at least a portion of the support grid being within the first region, wherein the support grid is operative for mechanically supporting the first support membrane, and wherein the support grid includes a plurality of windows that expose the first surface, and wherein the specimen layer is between the first etch-stop layer and the support grid.

13. The method of claim 9 further comprising forming a support grid on the substrate, at least a portion of the support grid being within the first region, wherein the support grid is operative for mechanically supporting the first support membrane, and wherein the support grid is between the first etch-stop layer and at least a portion of the specimen layer.

14. The method of claim 9 further comprising removing the first material within a second region by exposing the substrate to the first etchant, wherein the first material in each of the first region and the second region is exposed to the first etchant at the same time.

15. The method of claim 9 wherein the second material comprises a material selected from the group consisting of aluminum oxide, hafnium oxide, titanium oxide, zirconium oxide, nitrides including silicon nitride, tungsten nitride, and titanium nitride and wherein the additive process is selected from the group comprising atomic-layer deposition, atomic-layer epitaxy, molecular beam epitaxy, vapor-phase epitaxy, metal-organic chemical vapor deposition, chemical-vapor deposition, low-pressure chemical-vapor deposition, plasma-enhanced chemical-vapor deposition, evaporation, and sputter deposition.

16. An apparatus comprising an electron-microscopy support for supporting a specimen, wherein the electron-microscopy support includes:

a substrate comprising a first material, the substrate including a first cavity in a first region;

a first etch-stop layer disposed on the substrate, wherein the first etch-stop layer comprises a second material, and wherein the first etch-stop layer has a thickness that is less than or equal to 50 nanometers; and a first support membrane, wherein the first support membrane comprises a first portion of the first etch-stop layer, the first portion being in the first region.

17. The apparatus of claim 16 further comprising a second support membrane, wherein the second support membrane comprises a second portion of the first etch-stop layer, the second portion being in a second region.

18. The apparatus of claim 16 further comprising a support grid, the support grid being disposed on the substrate in the first region, wherein the support grid is operative for mechanically supporting the first support membrane, and wherein the support grid and substrate are monolithically integrated.

19. The apparatus of claim 16 wherein the substrate includes a first layer and a second layer, the first layer including a second cavity in the first region.

20. The apparatus of claim 16 wherein the first etch-stop layer is an atomic-layer-deposited layer.

* * * * *